United States Patent [19]

Sauter et al.

[11] Patent Number: 5,360,014
[45] Date of Patent: Nov. 1, 1994

[54] SIZING APPARATUS FOR HEART VALVE WITH SUPRA ANNULAR SUTURE RING

[75] Inventors: Joseph A. Sauter; Ronald S. Bell, both of Austin, Tex.

[73] Assignee: Carbomedics, Inc., Austin, Tex.

[21] Appl. No.: 150,595

[22] Filed: Nov. 10, 1993

[51] Int. Cl.⁵ ............................................. A61F 2/00
[52] U.S. Cl. ........................................ 128/774; 623/2
[58] Field of Search .................. 128/774, 780; 623/2; 33/511, 512, 514.1; 606/102, 194

[56] References Cited

U.S. PATENT DOCUMENTS

| | | | |
|---|---|---|---|
| 4,211,241 | 7/1980 | Kaster et al. | 33/512 X |
| 4,643,194 | 2/1987 | Fogarty | 33/512 X |
| 4,865,600 | 12/1989 | Carpenter et al. | 623/2 |
| 5,041,130 | 8/1991 | Cosgrove et al. | 623/2 |
| 5,163,955 | 11/1992 | Love et al. | 623/2 |
| 5,197,979 | 3/1993 | Quintero et al. | 623/2 |
| 5,236,450 | 8/1993 | Scott | 623/2 |

Primary Examiner—Sam Rimell
Attorney, Agent, or Firm—John R. Merkling

[57] ABSTRACT

A sizing apparatus for a supra-annular heart valve comprising a sizing probe mounted on a bendable shaft. The sizing probe comprises a cylindrical body with a proximal surrounding lip, the body and lip having a combined height equivalent to a similar height of the supra-annular heart valve. The body has an outside diameter which corresponds to that of the body of the supra-annular heart valve, and the lip has an outside diameter which corresponds to that of the sewing ring brim. Proximal from the lip is an annulus sizer having a shape corresponding to the interior opening or orifice of the selected heart valve. In use, the annulus sizer is placed in the aorta to pass through the annulus in the heart at the site of the excised natural valve, so that the attending physician will be able to recognize the largest permissible size for the supra-annular heart valve. A set of sizers is supplied corresponding to the different sizes of available heart valves.

8 Claims, 3 Drawing Sheets

SIZING APPARATUS FOR HEART VALVE WITH SUPRA ANNULAR SUTURE RING

BACKGROUND OF OUR INVENTION

Our invention is directed to a sizing apparatus for a prosthetic heart valve with an improved supra annular suture ring.

Mechanical artificial heart valves for humans are frequently fabricated from a form of carbon known commercially as Pyrolite TM carbon, a trademark of Carbomedics, Inc., the assignee of our present invention. Pyrolitic carbon is employed because of its unusual non-thrombogenic properties. Moreover, it is lightweight, hard and quite strong.

A standard implantable mechanical heart valve usually has an annular valve housing or body to provide a passageway for blood. Leaflets are mounted in the annular body and open or close the blood flow passageway. Usually there are one or two leaflets, but occasionally triple leaflet configurations have been proposed. On the outside of the valve body there is usually a circumferential groove. This groove is used to attach a suture ring to the valve body.

The suture ring is used to sew the heart valve to the patient's heart tissue. The ring generally comprises a knit fabric tube which is rolled into a toroidal form and which is secured about the heart valve body in the circumferential groove. Various methods and apparatus have been proposed for securing the suture ring to the heart valve. It is known, for instance, to bind the ring into the groove with a plastic thread. It has also been proposed to form a rotatable suture on the heart valve using heat shrinkable plastic material, as disclosed in U.S. Pat. No. 3,781,969. U.S. Pat. No. 3,491,376 suggests that a suture ring should be formed as a separate sub-assembly which should then be attached to the heart valve. In the '376 patent, the suture ring is described as including a resilient annular member which is temporarily deformed, so as to snap onto the valve body. U.S. Pat. No. 3,579,642 proposes the use of metal snap rings which must be radially expanded to place the suture ring about the valve body.

In U.S. Pat. No. 4,743,253, Magladry proposed a two-part suture ring comprising the knit fabric and an internal crescent-shaped ring which would be deformed inwardly by electromagnetic forming to clamp the heart valve while permitting relative rotation between the suture ring and the heart valve.

In U.S. Pat. No. 5,071,431, Campbell, et al. disclosed a suture ring comprised of essentially three parts: a stiffening ring which fits over an outer surface of a heart valve; a knit fabric sewing cuff attached to the stiffening ring, and a locking ring for securing the stiffening ring to the heart valve.

It has been found that the efficiency of a prosthetic heart valve is most dependent on the size of the valve. In other words, improved hemodynamic characteristics can be expected if the central orifice of the heart valve is made as large as possible with respect to the patient's anatomy. In the past, however, prosthetic heart valves have been implanted wholly or partially within the annulus of the excised natural valve. This strategy results in an effective reduction in the flow area by the combined amount of area taken up by the valve body wall, stiffening ring and suture ring.

To overcome this problem, a prosthetic heart valve can be used with a suture ring and stiffening ring combination which permits the prosthetic heart valve to be implanted above the site of the excised valve, for example, in the Sinus of Valsalva. Preferably, such a valve comprises an annular suture ring with a flared upstream edge having a smooth transition with an upstream edge of a heart valve. To use such a valve successfully, however, a sizer is needed.

SUMMARY OF OUR INVENTION

More than is the case with any other mechanical valve, a sizer for the supra-annular valve is an indispensable tool in assuring a proper fit of valve to patient. The supra-annular valve makes it possible to obtain a match between the native annulus and the inner diameter of the valve. Such a match is ideal since it minimizes the pressure gradient across the valve. The use of this valve, however, requires a consideration which is not necessary with an ordinary intra-annular valve. A surgeon implanting the supra-annular valve must consider the position of its superstructure relative to the physiology of the patient. Most notably, the surgeon must verify that there is sufficient clearance for the coronary arteries. The supra-annular sizer makes it possible for the surgeon to evaluate the ideal valve orifice match for the native annulus while simultaneously considering the clearance of the coronaries by the outer profile of the valve. This is because the lower section of the sizer is a cylinder which corresponds to the inner diameter of the valve orifice and the upper section is a model of the valve's outer profile. Clinical experience has demonstrated the importance of this sizer. In some cases, for example, the lower section of the sizer fit within the annulus, indicating that a particular size of valve could be employed, but, at the same time, the upper profiled section of the sizer demonstrated that a smaller valve had to be used to compensate for a condition of insufficient coronary clearance or aortic root size.

We have invented a sizing apparatus for a supra-annular heart valve comprising a sizing probe mounted on a bendable shaft. The sizing probe comprises a cylindrical body with a proximal surrounding lip, the body and lip having a combined height equivalent to a similar height of the supra-annular heart valve. The body has an outside diameter which corresponds to that of the body of the supra-annular heart valve, and the lip has an outside diameter which corresponds to that of the sewing ring brim. Proximal from the lip is an annulus sizer having a shape corresponding to the interior opening of the selected heart valve. In use, the annulus sizer is placed in the aorta to pass through the annulus in the heart at the site of the excised natural valve, so that the attending physician will be able to recognize the largest permissible size for the supra-annular heart valve. A set of sizers is supplied corresponding to the different sizes of available heart valves.

The object of our invention is to provide a sizing apparatus for use with supra-annular heart valves and in particular, a sizing apparatus which compares the available inter annular space to the orifice area of a supra-annular heart valve.

These and other features and advantages of our invention will be apparent from the following description, taken with the accompanying drawings.

DETAILED DESCRIPTION OF OUR PREFERRED EMBODIMENT

We will now describe our invention with reference to the accompanying drawings. Like numerals are used to designated like parts throughout.

Figure 1:
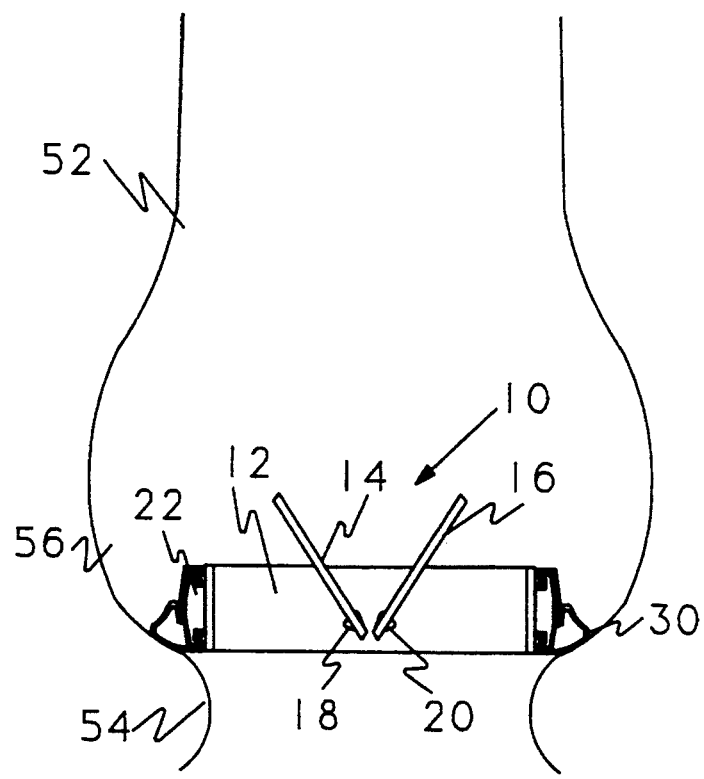
FIG. 1 is a cross sectional view of a supra-annular prosthetic heart valve.
Figure 2:
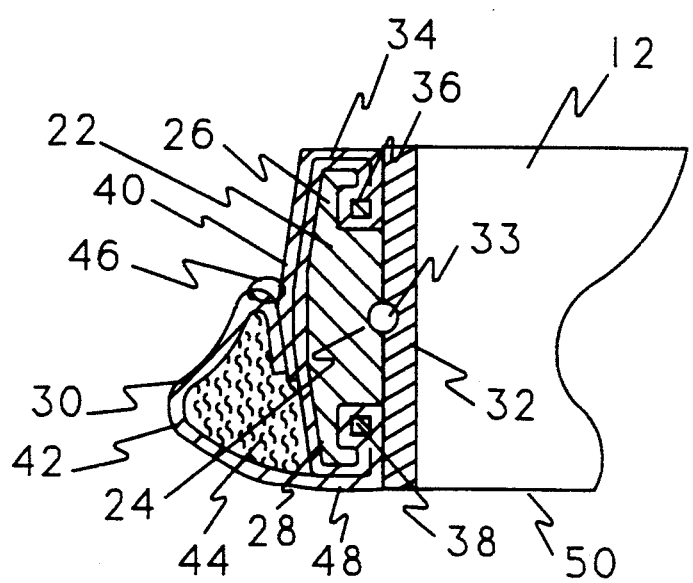
FIG. 2 is an enlarged cross sectional view of a part of the supra-annular heart valve.
Figure 3:
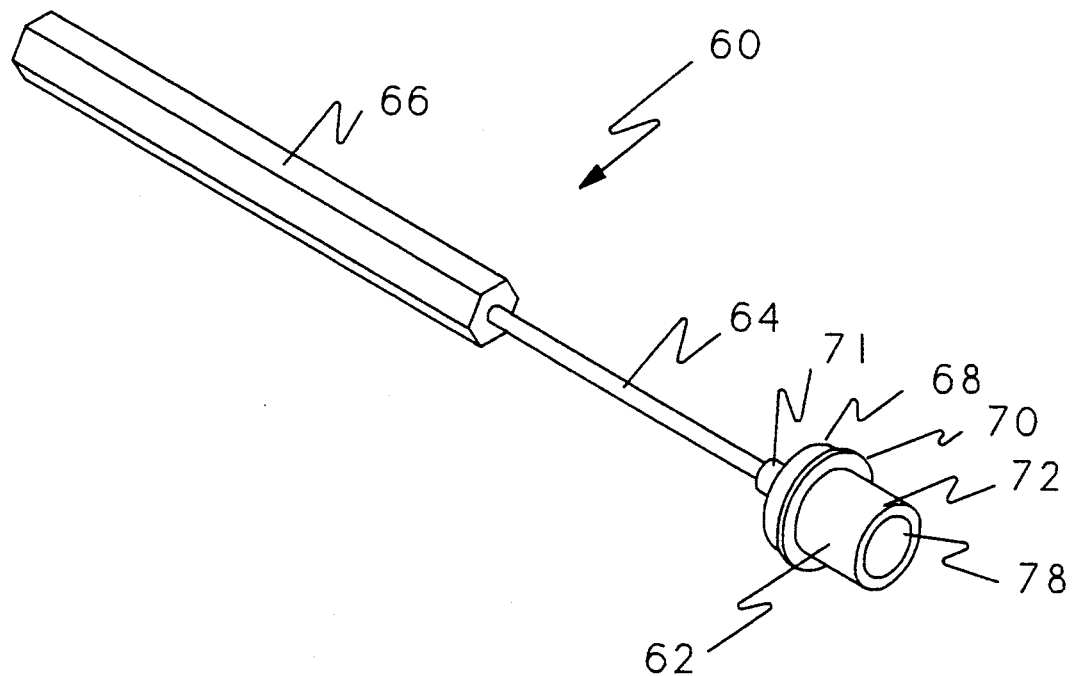
FIG. 3 is a perspective view of a sizer for use with the supra-annular heart Valve.
Figure 4:
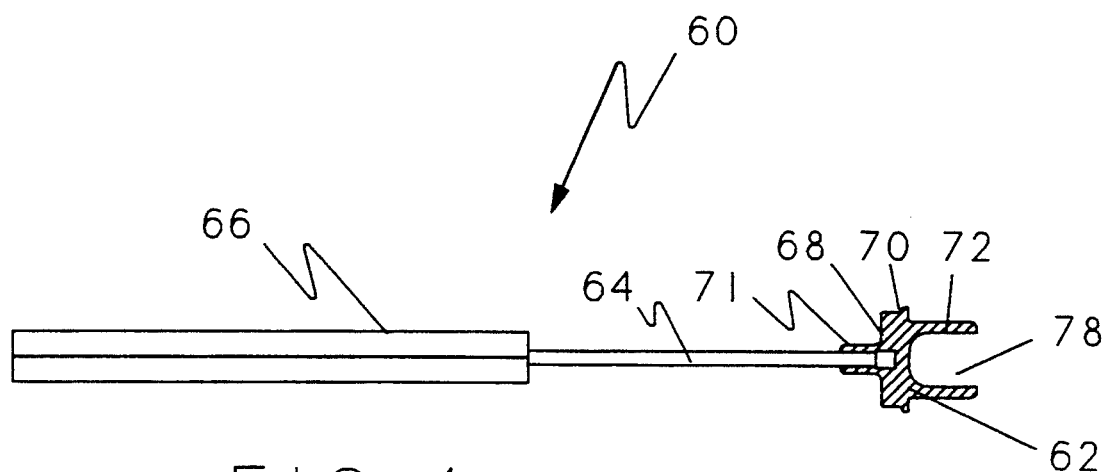
FIG. 4 is a plan view of the sizer of FIG. 3, in partial cross in section taken along line 4—4.

FIG. 1 illustrates a cross sectional view of a prosthetic heart valve with a supra annular suture ring. The supra-annular prosthetic heart valve is generally designated 10. The heart valve comprises an annular valve body 12 with two pivoting leaflets 14, 16. The leaflets 14, 16 have pivots, not shown, which engage recesses 18, 20. Two recesses are provided for each leaflet, as is known in the art. The annular valve body 12 and leaflets 14, 16 are comprised of pyrolitic carbon, for example Pyrolite ® carbon sold by Carbomedics, Inc., the assignee of our invention. This material is hard, durable and biocompatible. It is also relatively brittle and is frequently supported by a stiffening ring 22. As seen in FIG. 2, the stiffening ring 22 comprises a central body having an interior groove 24. An upper capture arm 26 and a lower capture arm 28 extend from the ring body 22 and provide means for capturing a suture ring 30. Other alternatives are also known to those skilled in the art.

An exterior groove 32 is provided on the annular valve body 12. A lock wire 34, placed between the annular valve body 12 and the stiffening ring 22, holds the stiffening ring and suture ring on the valve body. The lock wire is installed into mating semi-circular grooves in the stiffening ring and valve body through an opening in the stiffening ring.

The suture ring is comprised of a knitted fabric tube 34 which is held on the stiffening ring by a upper capture ring 36 and a lower capture ring 38. An upper free end 40 of the tube is brought down around the outside of the stiffening ring where it may be lightly sewed into a position. A lower end 42 of the tube is brought upward to form an area which can be sutured to the body. A filler 44 of, for example, texturized yarn, Teflon (TM) felt, molded silicon, woven fabric, or knit fabric can be contained within the lower end 42 to give the suture ring shape. The lower end 42 is stitched 46 in position to form the sewing ring.

In the supra-annular valve, the sewing ring 40 provides a surface 48 which is flush with an upstream or inflow edge 50 of the valve body 12. In FIG. 1, the heart valve 10 is shown in the ascending aorta of a patient at the aortic annulus 54. The aorta 52 comprises a valve and, downstream thereof, the Sinus of Valsalva 56. Other valves have been mounted totally or partially within the aortic annulus 54. Because the aortic annulus is below the supra-annular valve, it is not held open by the valve body. Consequently, proper sizing of the supra-annular valve is necessary so that tissue from the annulus will not occlude the opening in the valve. Moreover, the height of the valve must be considered, to avoid blocking the coronary openings which supply blood to the heart itself. In order to fill this need, we have invented a valve sizer 60 for use with supra-annular prosthetic heart valves, as described above.

Figure 6:
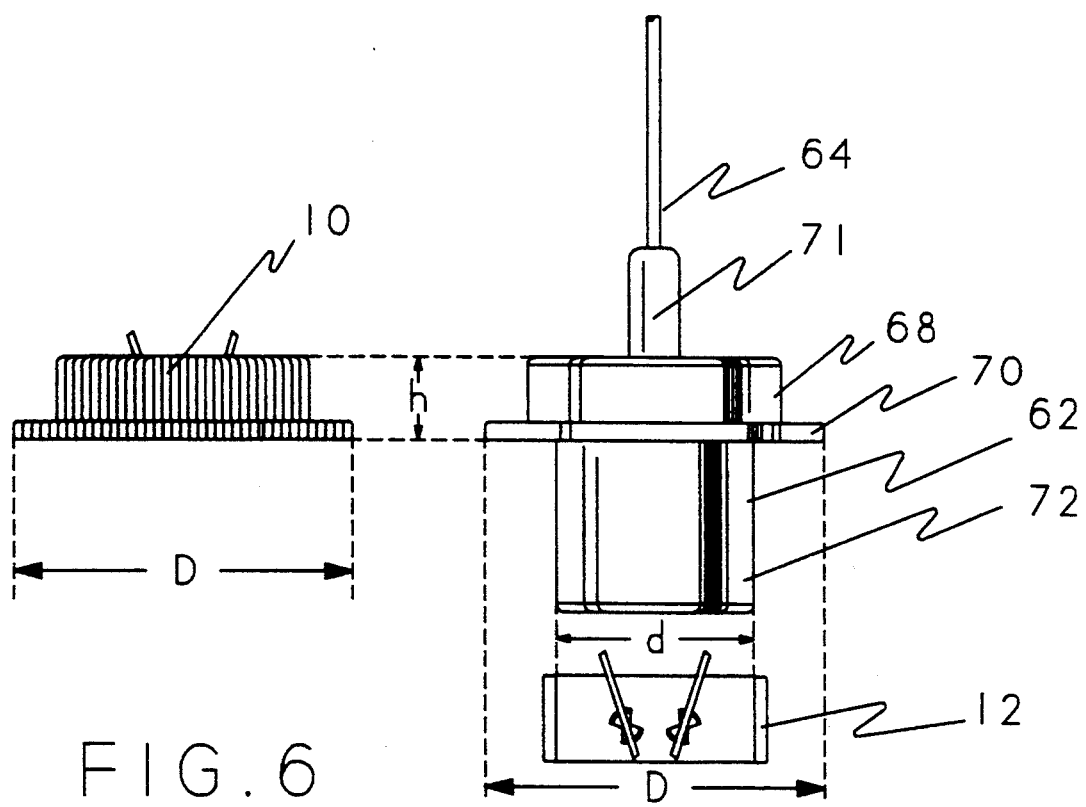
FIG. 6 is a plan view of the sizer with comparisons to the supra-annular heart valve.

The sizer 60, comprises a sizing probe 62 mounted on a bendable stainless steel shaft 64. The shaft 64 is connected to a handle 66 whereby the surgeon will be able to manipulate the sizing probe 62. Sizing probe 62 comprises a cylindrical body 68 with a proximal surrounding lip 70. As seen in FIG. 6, the body 68 and lip 70 have a combined height h which is equivalent to a similar height h of the supra-annular valve. Moreover, the lip 70 has a circular diameter D which likewise corresponds to an outer diameter D of the heart valve 10, including the sewing ring brim.

Figure 5:
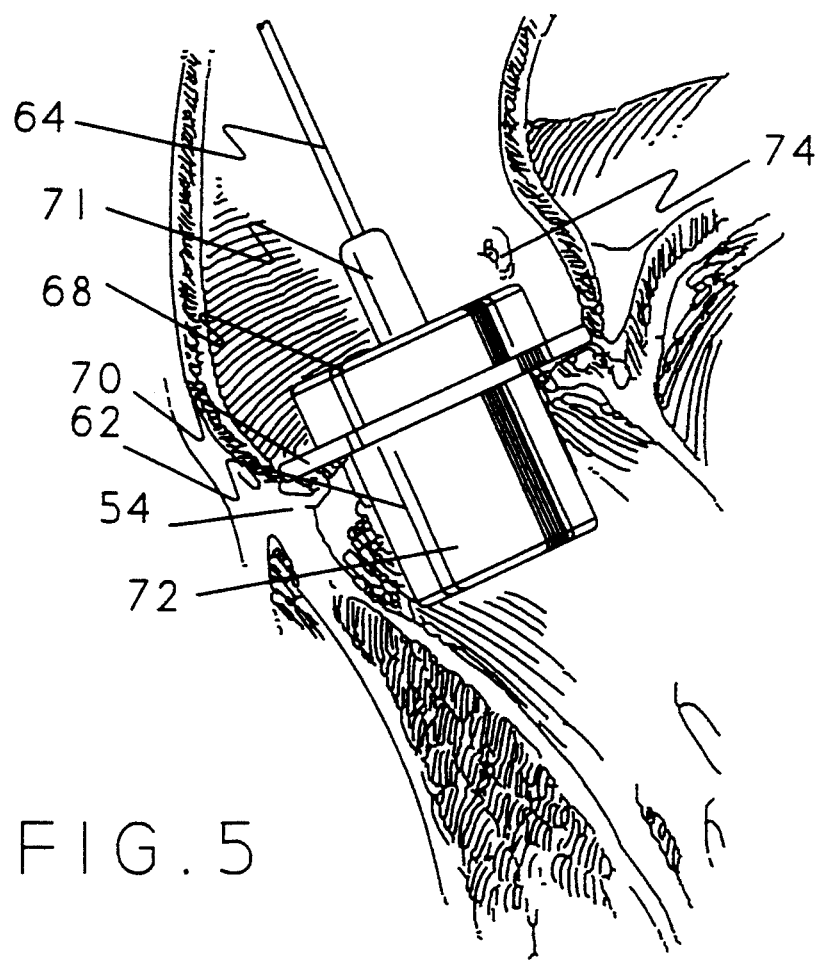
FIG. 5 is a perspective view of the sizer in use.

Distal from the body 68 is a molded shaft 71 which is provided to connect the sizing probe 62 to the shaft 64. Proximal from the lip 70 is an annulus sizer 72. The annulus sizer 72 is preferably cylindrical in shape and has a outside diameter d which corresponds to the inside diameter of the annular body 12 of the heart valve 10, as shown in FIG. 6. This dimension d is the effective opening available for the heart valve. As shown in FIG. 5, when the sizer 60 is in use, it is placed into the aorta such that the annulus sizer 72 passes into the annulus 54. Careful sizing is necessary so that, in use, the tissue of the annulus 54 will not occlude the valve 10. Moreover, because the height h of the sizer 60 corresponds to a similar h of the valve 10, it can be determined if the coronaries 74 which supply blood to the heart are clear. This use is also shown in FIG. 5. Thus, the sizer of our invention gives three critical dimensions: a diameter d which corresponds to the available opening in the annulus 54 and is to be matched by the interior diameter d of the annular valve body 12; an outside diameter D which corresponds to an outer diameter of the sewing ring of the heart valve 10 and a height h which corresponds to the overall height h of the sewing ring and annular body combination of the heart valve 10 and which should give clearance for the coronary arteries 74.

Because our preferred embodiment for a supra-annular valve comprises an annular valve body 12, we show the annulus sizer 72 as being essentially cylindrical in shape, corresponding to the opening or orifice in the annular valve body 12. However, other shapes, for example, ellipsoid, have been proposed for the openings of heart valves. Clearly, the circumferential shape of the annulus sizer 72 should correspond to the valve opening in the selected heart valve.

In constructing the sizer 60, we prefer to use a plastic substance for the handle 66 and for the sizing probe 62, while the shaft 64 is comprised of a stiff, but bendable metal. To mold the sizing probe 62 onto the shaft 64 we have provided a cavity 78 within the annulus sizer 72 so that the plastic would not deform during curing. If small volumes are manufactured, however, the cost of producing molds may not be justified. We have also made the sizing probe 62 out of stainless steel. The cavity 78 is still provided, to reduce the weight of the probe 62.

Those skilled in the art will recognize that our invention may be embodied in other specific forms without departing from the spirit or essential characteristics thereof. The foregoing description is intended, therefore, to be illustrative and not restrictive, and the scope of our invention is defined by the following claims. All changes which come within the meaning of equivalency of the claims are therefore intended to be embraced therein.

We claim as our invention:

1. An apparatus for determining the appropriate size of a supra-annular mechanical prosthetic heart valve, said heart valve having a height, a diameter orthogonal thereto and an orifice extending through said valve for passage of blood therethrough, said apparatus comprising a handle; and probe means mounted proximally from said handle, said probe means comprising a body portion having a height and a diameter orthogonal to said height, said height approximating the height of said supra-annular heart valve, a circumferential lip proximal from said body portion, said lip having a proximal edge for preventing said body portion from entering said site of said excised heart valve and having a constant diameter greater than said diameter of said body portion, said lip diameter approximating the diameter of said supra-annular heart valve; and an annulus portion extending proximally from said circumferential lip, said annulus portion having a side wall congruent with said orifice in said heart valve.

2. The apparatus according to claim 1 wherein said side wall of said annulus portion is substantially cylindrical.

3. The apparatus according to claim 1 further comprising a flexible shaft between said handle and said body portion.

4. The apparatus according to claim 3 wherein said side wall of said annulus portion is substantially cylindrical.

5. A method for determining the appropriate size of a supra-annular prosthetic heart valve, said heart valve having a height, a diameter orthogonal thereto and an orifice extending through said valve for passage of blood therethrough, said method comprising the steps of extending a sizing apparatus into a patient's circulatory system towards a site of an excised heart valve, said sizing apparatus comprising a handle; and probe means mounted proximally from said handle, said probe means comprising a body portion having a height and a diameter orthogonal to said height, said height approximating the height of said supra-annular heart valve, a circumferential lip proximal from said body portion, said lip having a proximal edge for preventing said body portion from entering said site of said excised heart valve and having a constant diameter greater than said diameter of said body portion, said lip diameter approximating the diameter of said supra-annular heart valve; and an annulus portion extending proximally from said circumferential lip, said annulus portion having a side wall congruent with said orifice in said heart valve;

inserting said annulus portion into an annulus at said site;

determining if said annulus portion substantially fills said annulus;

advancing said sizing apparatus until said body portion is adjacent said annulus;

determining if openings for the patient's coronary arteries are exposed above said height of said body portion;

withdrawing said sizing apparatus from the heart; and selecting for implantation a supra-annular heart valve having dimensions similar to said sizing apparatus.

6. The method according to claim 5 wherein said side wall of said annulus portion is substantially cylindrical.

7. The apparatus according to claim 5 further comprising a flexible shaft between said handle and said body portion.

8. The apparatus according to claim 7 wherein said side wall of said annulus portion is substantially cylindrical.

* * * * *